US005741679A

United States Patent [19]
George et al.

[11] Patent Number: 5,741,679
[45] Date of Patent: Apr. 21, 1998

[54] REGULATABLE NUCLEIC ACID THERAPEUTIC AND METHODS OF USE THEREOF

[75] Inventors: Shaji T. George; Andy Shih; Jeffrey Michael Bockman, all of New York, N.Y.

[73] Assignee: Innovir Laboratories, Inc., New York, N.Y.

[21] Appl. No.: 307,401

[22] Filed: Sep. 16, 1994

Related U.S. Application Data

[63] Continuation of Ser. No. 987,465, Dec. 4, 1992, abandoned.
[51] Int. Cl.$^6$ .............................. C12P 19/34; C07H 21/04
[52] U.S. Cl. ...................... 435/91.31; 435/23.1; 435/24.5
[58] Field of Search ..................... 435/91.31, 172.3, 435/320.1; 536/23.1, 24.5

[56] References Cited

U.S. PATENT DOCUMENTS

| 4,987,071 | 1/1991 | Cech et al. ................................. 435/91 |
| 5,225,337 | 7/1993 | Robertson et al. ................... 435/91.31 |

FOREIGN PATENT DOCUMENTS

| 89/05852 | 6/1989 | WIPO . |
| 92/01786 | 2/1992 | WIPO . |

OTHER PUBLICATIONS

Parker et al. (1992) Raven Press Ser. Mol. Cell. Biol. 1(Gene Regul.):55–70.
Stull et al. (1995) Pharm. Res. 12:465–483.
Altman, S., "Ribonuclease P: An Enzyme With a Catalytic RNA Subunit," in *Adv. Enzymol.* 62:1–36 (John Wiley & Sons, New York, 1989).
Bartel, D.P. et al., "Isolation of New Ribozymes From a Large Pool of Random Sequences", *Science*, 261:1411–1418 (1993).
Beaudry, A., et al., G., "Directed Evolution of an RNA Enzyme," *Science*, 257:635–641 (1992).
Bock, L. et al., "Selection of Single–Stranded DNA Molecules that Bind and Inhibit Human Thrombin," *Nature*, 355:564–566 (1992).
Branch, A., et al., "The Brotherhood of Circuit RNA Pathogens: Viroids, Circular Satellites, and the Delta Agent," *Semin. Virol.*, 1:143–152 (1990).
Branch, A., et al., "Efficient Trans Cleavage and a Common Structural Motif for the Ribozymes of the Human Hepatitis δAgent" *Proc Natl. Acad. Sci. USA*, 88:10163–10167 (1991).
Brown, J. et al., "Characterization of PRNAs from Thermophilic Bacteria," in *Keystone RNA Processing Meeting*, 55abs (Keystone, 1992).
Cech, T., "Ribozymes, Tools for Sequence–Specific Cleavage of RNA." *Editorial Comments*, 16:1–5 (U.S. Biochemicals Corp., Cleveland, 1989).
Edgington, S.M., "Ribozymes: Stop making Sense", *Biotech.*, 10:256–262 (1992).

Ellington, A.D., et al., "In Vitro Selection of RNA Molecules that Bind Specific Ligands," *Nature*, 346:818–822 (1990).
Ellington, A.D., et al., "Selection In Vitro of Single–stranded DNA Molecules that Fold into Specific Ligand–binding Structures," *Nature*, 355:850–852 (1992).
Famulok, M., et al., "*In Vitro* Selection of Specific Ligand–binding Nucleic Acids", *Angew Chem. Inst. Ed. Engl.*, 31:979–988 (1992).
Forster, A.C., et al., "External Guide Sequences for an RNA Enzyme," *Science*, 249:783–786 (1990).
George, S.T., et al., "Ribozyme Accessibility of Potential Cleavage Sites in Hepatitis B Virus S Gene Messenger RNA," *Abstracts: Molecular Biology of Hepatitis B Viruses*, 131 (La Jolla, CA, 1992).
Haseloff, J., et al., "Simple RNA Enzymes with New and Highly Specific Endoribunuclease Activities," *Nature*, 334:585–591 (1988).
Herschlag, D., et al., "DNA Cleavage Catalysed by the Ribozyme from Tetrahymena," *Nature* 344:405–409 (1990).
Kuo, M.Y.-P., et al., "Characterization of Self–Cleaving RNA Sequences on the Genome and Antigenome of Human Hepatitis Delta Virus," *Journal of Virology*, 62(12):4439–4444(1988).
Noller, H.F., et al., "Unusual Resistance of peptidyl Transferase to Protein Extraction Procedures," *Science*, 256:1416–1419 (1992).
Perotta, A.T., et al., "The Self–cleaving Domain from the Genomic RNA of Hepatitis Delta Virus: Sequence Reguirements and the Effects of Denaturant," *Nucleic Acids Res.*, 18(23):6821–6827 (1990).
Perotta, A.T., et al., "Pseudoknot–like Structure Reguired for Efficient Self–cleavage of hepatitis Delta Virus RNA," *Nature*, 350:434–436 (1991).
Puttaraiu, M., et al., "A Circular Trans–acting Hepatitis Delta Virus Ribozyme", *Nucl. Acids Res.*, 21(18):4253–4258 (1993).

(List continued on next page.)

*Primary Examiner*—George C. Elliott
*Assistant Examiner*—Robert Schwartzman
*Attorney, Agent, or Firm*—Arnall Golden & Gregory, LLP

[57] ABSTRACT

Regulatable RNA molecules such as regulatable ribozymes, nucleic acids encoding such regulatable ribozymes, and methods of making and using such regulatable ribozymes are disclosed. Regulatable ribozymes comprise a ligand-binding RNA sequence and a ribozyme sequence capable of cleaving a separate targeted RNA sequence, wherein upon binding of the ligand to the ligand-binding RNA sequence, the activity of the ribozyme sequence against the targeted RNA sequence is altered. The ligand may be either an inorganic or an organic molecule and may be a co-drug which can be administered to specifically regulate the ribozyme activity. Regulatable RNA molecules other than ribozymes are also disclosed, such as regulatable mRNA molecules which comprise a ligand-binding RNA sequence separate from the coding sequence, wherein upon binding of a ligand to the ligand-binding RNA sequence, translation of the regulatable mRNA is altered.

28 Claims, 11 Drawing Sheets

OTHER PUBLICATIONS

Perotta, A.T., et al., "Cleavage of Oligoribunucleotides by a Ribozyme Derived from the Hepatitis δVirus RNA Sequence," *Biochemistry*, 31:16–21 (1992).

Piccirilli, J.A., "Aminoacyl Esterase Activity of the Tetrahymena Ribozyme," *Science*, 256:1420–1424 (1992).

Robertson, D., et al., "Selection In Vitro of an RNA Enzyme that Specifically Cleaves Single-Stranded DNA," *Nature*, 344:467–468 (1990).

Rosenstein, S.P., et al., "Self-cleavage of hepatitis Delta Virus Genomic Strand RNA is Enchanced under Partially Denaturing Conditions," *Biochemistry*, 29:8011–8016 (1990).

Sharmeen et al., "Antigenomic RNA of Human Hepatitis Delta Virus Can Undergo Self-cleavage," *J. Virol.*, 62:2674–2679 (1988).

Shih et al., "Efficient Trans-cleavage and Re-targeting of hepatitis Delta Virus Ribozymes," *Abstracts: Molecular Biology of Hepatitis B Viruses*, 130 (La Jolla, CA, 1992).

Smith, J.B., et al., "Antigenomic Hepatitis Delta Virus Ribozymes Self-cleave in 18 M Formamide,"*Nucleic Acids Research*, 19(6):1285–1289 (1991).

Symons, R.H. et al., "Ribozymes," *Critical Reviews in Plant Sciences*, 10(3):189–234 (CRC Press, Inc., Boca Raton, Fla. 1991).

Szostak, J.W., "In Vitro Genetics," *Trends Biochem Sci.*, 17:89–93 (1992).

Uhlenbeck, O.C., "A Small Catalytic Oligoribonucleotide," *Nature*, 328:596–600 (1987).

Weizsacker, F. von., et al., "Cleavage of hepatitis B Virus RNA by Three Ribozymes Transcribed from a Single DNA Template," *Biochem. Biophys. Res. Comm.*, 189(2):743–748 (1992).

Wu, H–N, et al., "Reversible Cleavage and Ligation of Hepatitis Delta Virus RNA," *Science*, 243:652–655 (1989).

Wu, H–N et al., "RNA Conformational Requirements of Self-cleavage of Hepatitis Delta Virus RNA," *Mol. Cell. Biol.*, 10(10):5575–5579 (1990).

Wu, H–N, et al., "Human Hepatitis δVirus RNA Subfragments Contain an Autocleavage Activity," *Proc. Nat. Acad. Sci. USA* 86:1831–1835 (1989).

Yarus, M., "Specific Amino Acid Binding Site Composed of RNA", *Science*, 240:1751–1758 (1988).

Yarus, M., "Specificity of Arginine Binding by the Tetrahymena Intron", *Biochem.*, 28:980–988 (1989).

Yuan, Y., et al., "Targeted Cleavage of mRNA by Human RNase P," *Proc. Nat. Acad. Sci. USA*, 89:8006–8010 (1992).

Zaug, A.J., et al., "The Intervening Sequence of RNA of Tetrahymenal is an Enzyme," *Science*, 231:470–475 (1986).

Rossi et al. In "Innovations in antiviral development and the detection of virus infection", Ed. T. Block et al., Plenum, N.Y, 1992, pp. 95–109.

Yarus (1988) Science 240:1751–1758.

Yarus (1989) Biochemistry 28:980–988.

Famulok et al. (1992) Angew Chem Int Ed Engl 31:979–988.

Science 262:1512–1514, Dec. 1993.

Rossi et al. In "Innovations in Antiviral Development & the Detection of Virus Infection", Ed. T. Block et al. Plenum, N.Y. 1992, p. 95–109.

LIGAND (20)

14B
14A 14C

TARGET RNA (24)

RIBOZYME ACTIVE WHEN LIGAND IS BOUND

FIG. 1d

TARGET RNA (24)

RNAT MOLECULE WITH BOUND LIGAND (30)

LIGAND (20)

RIBOZYME INACTIVE WHEN LIGAND IS BOUND

FIG. 3a

Regulatable Ribozyme against Hepatitis B virus RNA

Cibacron Blue-Binding Sequence (bold)
(5')GAGAAGCCCACCUGGCUUUGAACUCUAUGUUAUUGGGUGGGGGAAA
CUUAAGAAAACUACCACCCUUCAACCAUUACCGCCCUUCAGCCUGCCAG
CGCC<u>*CGAGUCUACUGAUGAGUCCGUGAGGACGAAACUCUGCGG*</u>(3')
Hammerhead Ribozyme Sequence (underlined italics)

REGULATABLE NUCLEIC ACID THERAPEUTIC AND METHODS OF USE THEREOF

This is a continuation of application Ser. No. 07/987,465, filed on Dec. 4, 1992, now abandoned.

BACKGROUND OF THE INVENTION

This invention relates to a method and composition for cleavage of RNA using regulatable ribozymes.

Ribozymes are defined as RNA molecules having enzyme like activity. There are three general pathways of RNA catalyzed cleavage: cleavage by viroid-like RNA, cleavage by RNAase P or the RNA component of RNAase P, the work of Sidney Altman at Yale University, and cleavage by the Tetrahymena ribozyme, the work of Thomas Cech at the University of Colorado. All naturally occurring ribozymes known to date, with the exception of RNAase P, work in cis and must be engineered to work in trans, i.e., on another molecule. This is accomplished by separating the portion of the RNA molecule with enzymatic activity from the portion serving as substrate, and conferring substrate-like properties, including appropriate sequences and appropriate secondary and tertiary structure, on the target molecule which is to be cleaved. Specificity can be conferred by adding complementary nucleic acid sequences which hybridize near the site to be cleaved on the target molecule.

Each class of ribozyme cleaves a different sequence of nucleotides using distinct mechanisms of action. Moreover, each class is further distinguished based on how many nucleotide bases are essential for enzymatic activity and to the extent the intended target and the ribozyme can be manipulated to alter specificity.

M1 RNA, the RNA ribozyme subunit of *E. coli* RNAase P, is a nearly 400-base RNA molecule which cleaves precursor transfer RNAs to produce mature tRNAs. Other molecules can be converted into substrate for M1 RNA or RNAase P through the use of an external guide sequence characterized as an isolated oligoribonucleotide having at its 5' terminus at least seven nucleotides complementary to the nucleotides 3' to the cleavage site in the RNA to be cleaved and at its 3' terminus the nucleotides N C C A directly joined to the complementary nucleotides, wherein N is any nucleotide and the complementary nucleotides in the oligoribonucleotide hybridizes to the complementary nucleotides in the RNA to be cleaved, as described by Foster and Altman, et al., in *Science* 249:783–786 (1990), "External Guide Sequences for an RNA Enzyme". Yuan, Hwang, and Altman, *Proc. Natl. Acad. Sci.* 89 (17):8006–8010 (1992), "Targeted Cleavage of Messenger RNA by Human RNase P," recently described the construction of an external guide sequence for the eukaryotic equivalent of the *E. coli* RNAase P, based on a structure derived from a precursor tRNA.

There are several kinds of viroid-like RNA ribozymes found in plants and animals. The plant viroid-like ribozymes can be engineered to be as small as 20 nucleotides. The central motif is a characteristic conserved sequence that Uhlenbeck published in *Nature* 328:596–600 (1987), in which he proposed that all hammerheads shared certain features. The mechanism of the viroid-like ribozymes creates a 2', 3' cyclic phosphate and a 5' hydroxyl terminus.

The recent discovery of these catalytic RNAs provides a mechanism for new approaches to the treatment of diseases with an RNA-based pathogenesis; i.e., diseases resulting from the presence of a new RNA which might be of exogenous origin, e.g., viral or bacterial, or of endogenous origin, e.g., the expression of a novel RNA or the over-exposed expression of a pre-existing RNA. The theoretical advantage of ribozymes over antisense technology, for example, resides in their catalytic behavior. A target pathogenetic RNA will be cleaved by the particular ribozyme, irreversibly inactivating the RNA's biological activity, after which "turnover" occurs, dissociation of the ribozyme from the cleavage products and association with another target RNA molecule.

This very advantage of ribozymes, however, might prove to be a disadvantage in circumstances, for example, where the pathology results from over-expression of a cellular gene where what is desired for treatment of the disease is a reduction of message to the proper level and not elimination of the message or death of the particular cell. Such over-expression is one of the mechanisms of oncogenesis, where a normal cellular gene involved in cell growth becomes deregulated through over-expression or expression of an altered form amidst a background of the normal form from the other chromosome. In such cases one might wish to inactivate only a certain proportion of the target RNA in a diseased cell, returning the level of message to that steady-state level pre-existing in the healthy cell. A therapeutic such as a ribozyme whose activity, that is, its rate of inactivation of the target RNA, could be regulated through end-product feedback inhibition or exogenous administration or cessation of administration of an innocuous "co-drug", would allow the environmentally-responsive control of therapy in a deliberate and continually adjustable manner.

Recent work has demonstrated the remarkable diversity of catalytic function which RNA molecules can perform besides cleavage of other RNA molecules. Robertson and Joyce, *Nature* 344:467, 1990; Ellington and Szostak, *Nature* 346:818, 1990; Piccirilli, et al., *Science* 256:1420, 1992; Noller, et al., *Science* 256:1416, 1992; Ellington and Szostak, *Nature* 355:850, 1992; Bock, et al., *Nature* 355:564, 1992; Beaudry and Joyce, *Science* 257:635, 1992; Oliphent, et al., *Mol. Cell. Biol.* 9:2944, 1989; the teachings of which are specifically incorporated herein. RNA molecules with a given function, catalytic or ligand-binding, can be selected for from a complex mixture of random molecules in what has been referred to as "in vitro genetics" (Szostak, *TIBS* 19:89, 1992). One synthesizes a large pool of RNA molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992). Catalytic DNA molecules may also be found.

It is therefore an object of the present invention to provide ribozymes whose catalytic activity can be regulated or controlled by the presence of ligands which bind to the ribozyme and affect the binding to or cleavage of the target nucleic acid.

It is a further object to provide methods of use for regulatable ribozymes.

SUMMARY OF THE INVENTION

Construction of a regulatable ribozyme is described in which a ribozyme sequence is linked to a ligand-binding sequence, placing the activity of the ribozyme under the control of that ligand and requiring the presence of the ligand for activation or inactivation. RNA molecules are constructed in which one portion is capable of binding a ligand and the other portion is a ribozyme. After the selection of molecules which bind the ligand, a second selection process occurs in which the ligand-binding molecules are assayed for their catalytic function in the presence and absence of the ligand or "co-drug." In this manner regulatable ribozymes are selected for use in cleaving a target RNA in the presence of a ligand, or in cleaving a target RNA in the absence of a ligand.

This method and regulatable ribozymes are useful in cleaving a target RNA molecule in a controlled fashion. It is particularly useful when the target RNA molecule is present in a cell where it is not desirable to kill the host cell by complete inactivation of these RNA molecules.

BRIEF DESCRIPTION OF THE DRAWINGS

FIGS. 1A, 1B, 1C, and 1D are schematics of regulatable nucleic acid therapeutics.

FIGS. 2A and 2B are schematics of the process of cleaving a targeted RNA in a cell using a regulatable ribozyme which is inactive when not bound to ligand.

DETAILED DESCRIPTION OF THE INVENTION

A method and compositions are described for controlled cleavage of targeted RNA molecules using a ribozyme that can be regulated through the presence, or absence, of a ligand. In one case the ribozyme is active in the presence of a ligand, in the other case the ribozyme is inactive in the presence of a ligand.

This method is useful in situations where the target RNA is essential to cell viability and only a reduction of that RNA's level of expression is desired, rather than complete inactivation or elimination. For example, one proposed mechanism of oncogenesis is the over-expression of a cellular gene, such as one involved in regulation of the cell cycle of growth and proliferation. One might not be able to specifically deliver a ribozyme only to the tumor cells, but may also have delivery to the normal cells from which the tumor arose. The goal then is to re-regulate the tumor cells but not the normal cells. If the ribozyme is regulatable and active only in the presence, for example, of the over-expressed protein product of the cellular gene, then efficient cleavage of the corresponding RNA will only occur when the concentration of this protein is at a level sufficient to all binding to every ribozyme molecule. As the level of RNA falls due to ribozyme cleavage, the protein level should fall, resulting in some proportion of ribozyme molecules with no protein bound and therefore in an inactive conformation. Ultimately, some equilibrium will be reached between ribozyme inactivation and RNA synthesis. Alternatively, if the delivery of the ribozyme was non-specific, one might activate the ribozyme by the administration of a "co-drug" which might be preferentially taken up by rapidly proliferating cells such as tumor cells, attaining a higher concentration in such cells. The ribozyme can be targeted to an essential cellular gene and be active only in the presence of this co-drug. When the tumor mass has been sufficiently reduced or eliminated, administration of the co-drug would cease and any ribozyme present in normal cells would become inactive.

Another example is the situation in hepatocellular carcinoma associated with hepatitis B infection. Evidence suggests that the virus genome, which is integrated into the host cell DNA in liver cells, is responsible for the conversion of that cell into a tumor cell. This can be by expression of viral genes, the surface antigen or a trans-activating factor hbx, or a consequence of the integration itself. In the latter case, inactivation of viral gene expression by ribozyme cleavage of the surface antigen or hbx would have no effect. What is desirable is ribozyme cleavage of an RNA essential to cell survival so that the cell dies. However, the delivery process is often non-specific, so that the ribozyme could be delivered to cells not harboring the virus, which would be killed also. If the ribozyme is active only in the presence of the surface antigen protein or hbx protein, then only those cells with virus would be killed.

Conversely, the regulatable ribozyme system can be devised so that the ribozyme is only active in the absence of the ligand. One can design a form of regulatable gene therapy where the cellular disorder results from the inappropriate expression of a repressor protein which acts to shut-off cellular product important in proper cell functioning. Unrestricted ribozyme cleavage of the mRNA of the repressor might in itself also lead to aberrant cellular behavior. However, if the ribozyme is regulated by the protein product of the repressed gene, that is, inactive in its presence, then the system becomes self-regulating. As the level of repressor protein falls due to ribozyme cleavage of its mRNA, the repressed gene becomes de-repressed, and its protein expressed. When the concentration of this protein reaches a certain threshold, the ribozyme molecules are all bound to the ligand and inactivated.

Method for Construction of Regulatable Ribozymes

Ribozymes that can be regulated can be prepared and isolated by the method described below. Appropriate oligonucleotides are synthesized on an Applied Biosystems Incorporated (ABI, 850 Lincoln Center Dr., Foster City, Calif. 94404) Model 392 synthesizer using company reagents. The general design criteria is described below with reference to the figures. These are all subject to modifications and variations which do not alter the functionality of the ribozymes.

Figure 1A:
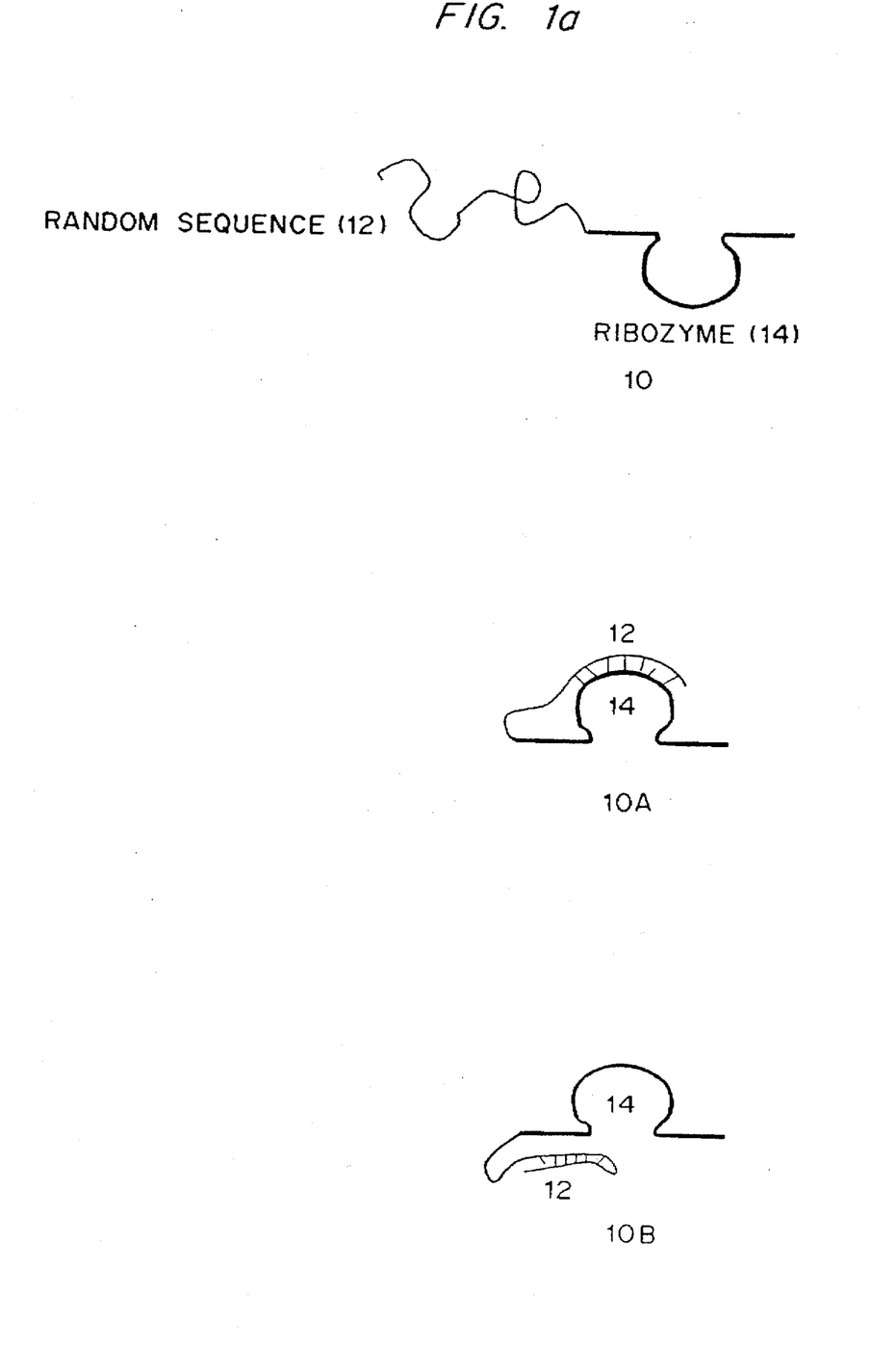
FIG. 1A is a schematic of the regulatable ribozyme components and some possible conformations.

As shown in FIG. 1A, nucleic acid molecules 10 synthesized containing a random sequence 12 and a defined ribozyme sequence 14 directed against a given target RNA (not shown) form a complex mixture of varied conformations 10a, 10b. Although the ribozyme sequence 14 is defined, the conformation of the entire molecule 10, including the ribozyme portion 14, is determined by the interaction of the random sequence 12 with itself and the ribozyme sequence 14.

Figure 1B:
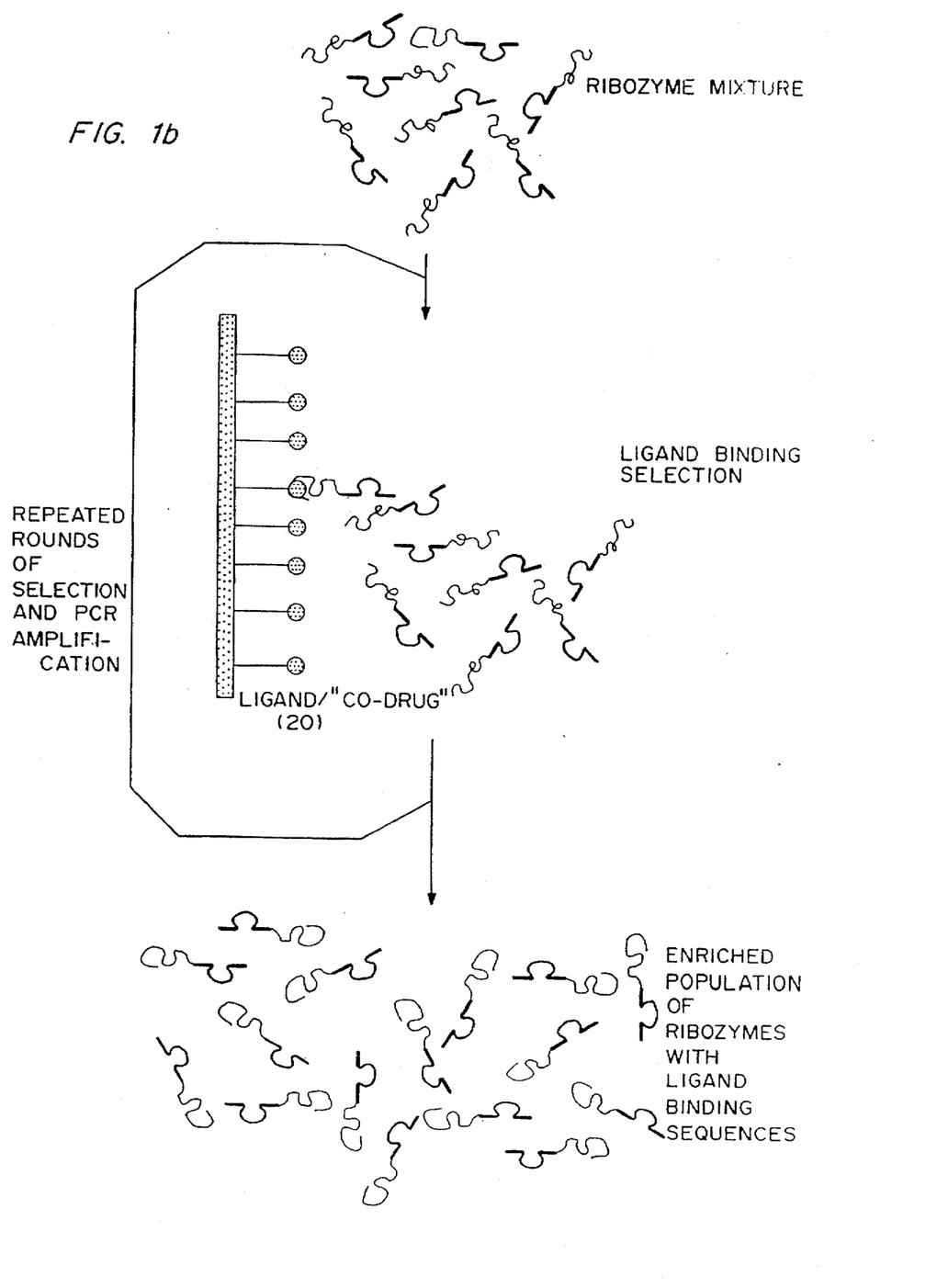
FIG. 1B is a schematic of the method for isolating regulatable ribozymes that bind a specific ligand.

To select for those molecules 10 which fold into a conformation which binds a desired ligand 20, such as a small organic molecule of sufficient complexity to allow binding, or a macromolecule such as a protein, the complex mixture of RNA molecules 10a, 10b, etc., is subjected to repeated rounds of affinity chromatography and PCR amplification in order to enrich for the ligand-binding molecules, as described by Bendry and Joyce, 1992. As depicted in FIG. 1B, this is accomplished by immobilizing the ligand on an inert substrate, amplifying the molecules 10 which are able to bind ligand using PCR or an equivalent methodology, under conditions promoting mutagenesis of the molecules 10, exposing the amplified mixture to the immobilized ligand under conditions allowing any potential binding between the molecules 10 and the ligand 20 to occur, removing material that does not bind, and repeating the amplification process. After several such cycles a population of RNA results in which virtually every molecule can bind the ligand.

Mutations can be introduced by use of a set of mutagenic oligodeoxynucleotides that contain random substitutions at a fixed frequency of occurrence. These partially randomized oligonucleotides are produced on an automated DNA synthesizer with nucleoside 3'-phosphoramidite solutions doped with a small percentage of incorrect monomers. Additional mutations are introduced after each round of selective amplification by performing the PCR under mutagenic conditions. The RNAs obtained by selective amplification are subjected to reverse transcription, the resulting cDNAs are PCR amplified, and the PCR products are transcribed to produce a progeny distribution of mutant RNAs.

Figure 1C:
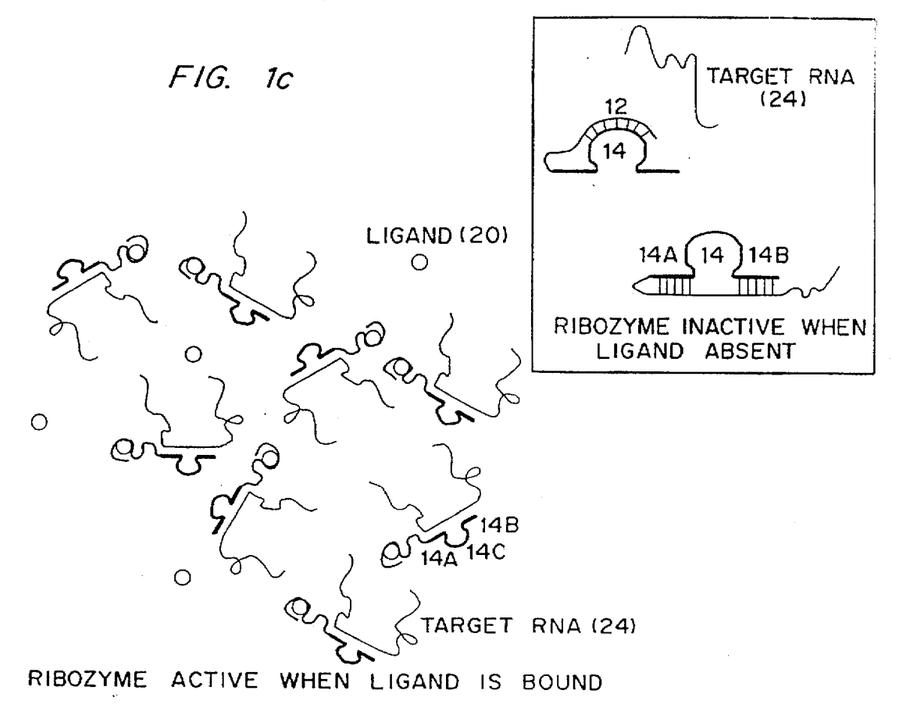
FIG. 1C is a schematic of regulatable ribozyme which is catalytically active when bound to ligand.

As shown in FIG. 1C, a certain number of molecules 10 should fold in such a way as to inactivate the ribozyme portion 14. This results in one case from stearic hinderance of the ability of the arms 14a, 14b of the ribozyme portion of the molecule to bind to the target RNA 24, and in another by alteration of the conformation of the catalytic core of the ribozyme 14c, which inhibits cleavage. This inhibition or inactivation of the ribozyme activity of the molecule 10 is relieved by subsequent binding of a co-drug (or ligand) 20.

Figure 1D:
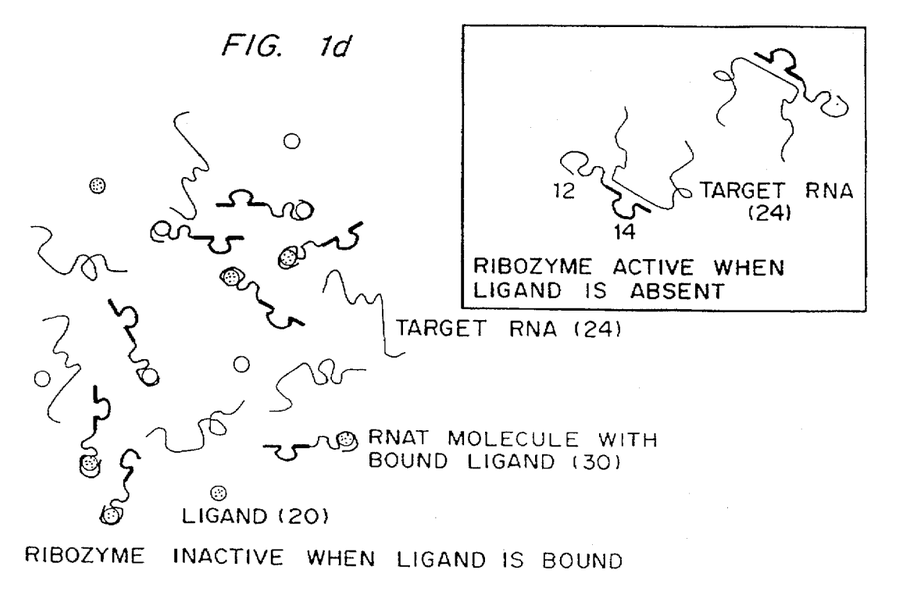
FIG. 1D is a schematic of regulatable ribozyme which is catalytically inactive in the presence of ligand.

Alternatively, as shown in FIG. 1D, a certain number of molecules 30 will fold into the inactive conformation only in the presence of a ligand 20, and in its absence fold into a catalytically active conformation 31.

The population of ligand-binding RNAs is then screened for activation or inactivation of the ribozyme by the co-drug ligand. The selection can be accomplished in at least two ways. In the first case, the pure population of ligand-binding RNA molecules is converted to double-stranded DNA via reverse transcriptase and then cloned into an in vitro expression vector. Individual bacterial transformants bearing a cloned sequence are grown up, the recombinant plasmid purified and the gene encoding the ligand-binding/ribozyme RNA transcribed. The homogeneous RNA from each clone is then assayed for cleavage in the presence or absence of the ligand.

This process can be simplified to reduce the total number of clones which must be isolated and transcribed and assayed, for example, by performing limiting dilution of the complex pool of ligand-binding molecules. From the concentration of RNA and the known size of the molecules, the number of molecules per unit volume, that is, the Molarity of the RNA solution, can be easily determined. Dilutions of the RNA can be made to statistically favor, for example, 10 RNA molecules per assay well. In 100 microtiter plates (96 well), approximately 105 molecules could be assayed for cleavage. Ellington and Szostak (1990) estimated there would be 1 in $10^{10}$ RNA molecules folded in such a way as to bind a given ligand in the original population of $10^{15}$ different sequences and that there were $10^2$ to $10^3$ different sequences in the final preparation. After purification for ligand-binding, virtually 100% of the molecules bind ligand. If only one molecule out of the $10^5$ different ligand-binding molecules had the ribozyme activated or inactivated by the presence of ligand, this method would allow isolation of that molecule. Because the ligand-binding RNAs have been enriched for by PCR in the cycles of affinity chromatography in the order of $10^{10}$-fold, ligand-regulated ribozymes present at much lower percentages would still be capable of isolation without undue experimentation. Those wells in which cleavage occurs in the presence or absence of the co-ligand are PCR amplified and cloned and the transcripts of individual clones assayed for inactivation or activation by ligand.

The methodology above can be modified to allow detection of pathogenic molecules or macromolecules other than nucleic acid, such as proteins. The ribozyme is linked to sequences which have been selected to both bind a non-nucleic acid ligand, such as a protein, and, when bound, to place the entire sequence of ribozyme plus ligand binding region into a conformation in which the ribozyme is active.

The ribozyme is designed to cleave a specific targeted RNA molecule. A variety of ribozymes can be utilized, ranging from hammerhead and axehead (HDV) ribozymes and Tetrahymena ribozymes, to RNAase P. RNAase P is endogenous to all procaryotic and eukaryotic cells and can be directed to cleave a targeted RNA molecule using an external guide sequence. As used herein, the ribozyme component of the regulatable ribozyme is used to mean a ribozyme or an external guide system (EGS) in a system containing RNAase P (or M1 RNA, the procaryotic RNA component of the RNAase P), where the RNAase P can be attached to the EGS or separately in solution. Cleavage of the targeted sequence is dependent on the selection of the ribozyme. For example, if the ribozyme is derived from newt satellite RNA, the cleavage site follows NUX, where N=any nucleotide, X=any nucleotide except G, and U is uridine.

The Random Sequence

There is no set number of base pairs for hybridization or binding to ligand or the length of base pairs between random RNA-ribozyme molecule and target RNA, since these will vary with each ribozyme system and targeted RNA. However, in general the random sequence will contain between 20 and 100 nucleotides, selected as described above for binding to a specific ligand. Although referred to herein as a "random" sequence, it is understood that the sequence is random only as originally used in the selection process, that the product of the selection process is not random but a set of specific sequences which bind specifically to a defined ligand.

Selection of the Ligand

The ligand can be a nucleic acid molecule, a protein, polysaccharide or sugar, or an organic or inorganic molecule. The nature of the ligand can be chosen to be exogenously supplied, such as some non-toxic molecule or drug which readily enters at least the cells containing the targeted RNA, or alternatively, an entirely endogenous system can be designed in which the controlling ligand is some small metabolite or macromolecule within the target cell which is directly or indirectly related to the pathology to be corrected. For example, the protein encoded by the target RNA could be the ligand. The activity of the regulatable ribozyme is dependent on binding to the pathogenetic protein. As the level of target RNA falls due to cleavage by the ligand-activated ribozyme, the concentration of protein ligand falls. When the concentration falls below that at which the regulatable RNA molecules are all occupied, the rate of ribozyme cleavage will begin to fall off. By selecting for differing ribozyme-ligand affinities, the appropriate level of regulation of ribozyme-mediated destruction of the target RNA can be achieved for any given situation.

Selection of the Target RNA Molecule

The target RNA is selected so that cleavage of the target RNA inhibits a pathogenic process arising either as a result of the presence and expression of the RNA molecule, or which is essential for viability of the cell. For example, the RNA could be mRNA encoding an essential protein component of a bacterial or viral pathogen. The RNA could be bacterial or viral RNA essential to infection or replication of the bacteria or virus, particularly, for example, in the case of RNA viruses. The RNA could be transcribed from a tumor oncogene or encode a tumor-specific protein. The RNA could encode a defective protein, such as the defective hemoglobin molecules characteristic of sickle cell anemia.

The present invention will be further understood by reference to the following non-limiting examples.

EXAMPLE 1

Inhibition of Protein Production with Regulatable Ribozyme

Figure 2A:
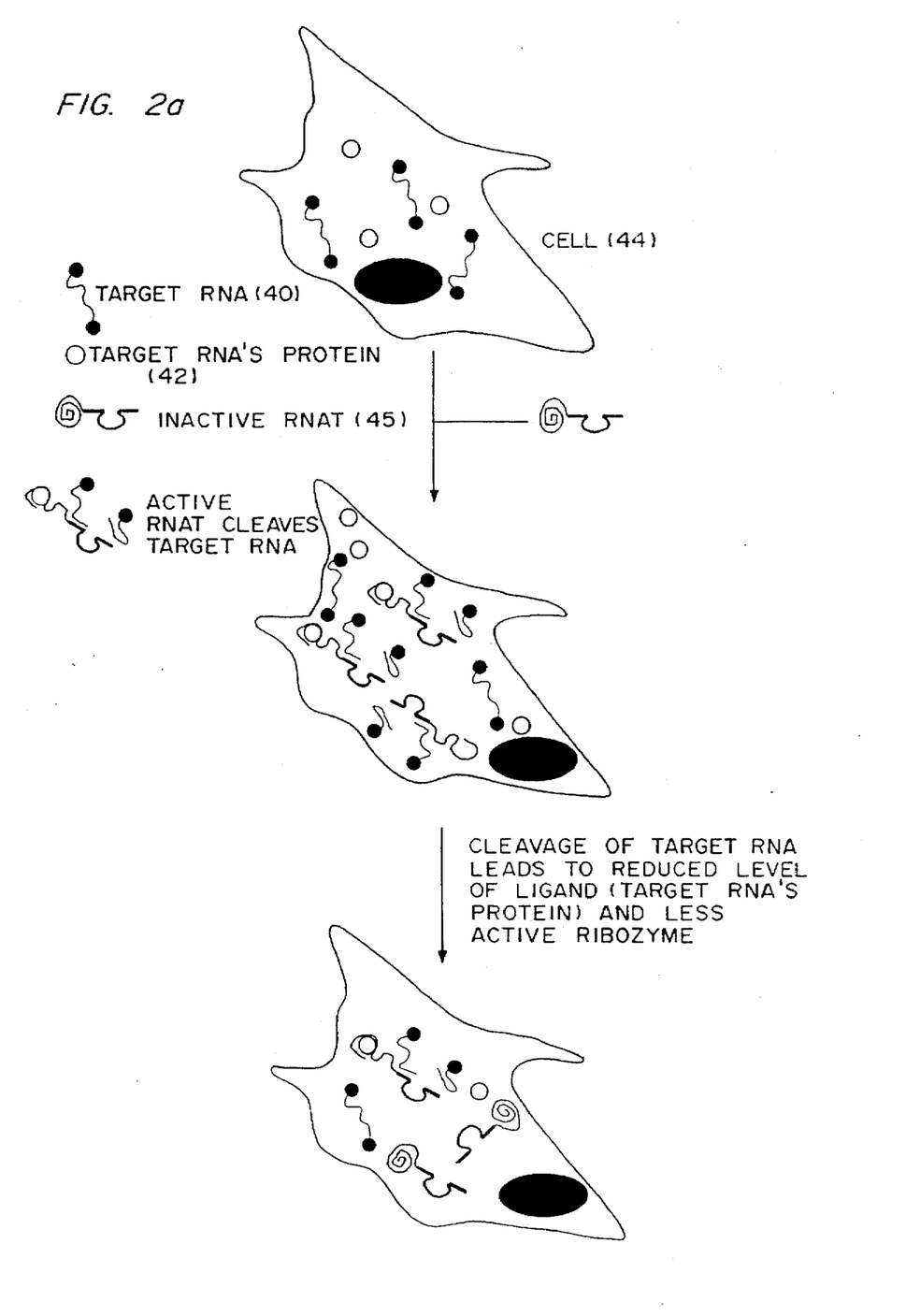
FIG. 2A is a system where the protein encoded by the target RNA positively regulates the activity of the ribozyme cleaving that RNA.

As shown in FIG. 2A, a regulatable ribozyme was constructed as shown above, to cleave a target RNA 40 encoding a target RNA protein 42 in a cell 44, as shown in FIG. 2. The activity of the regulatable ribozyme molecule 45 is dependent on binding to the protein 42, so that the ribozyme 45 is active only when bound to protein 42. As the level of target RNA 40 falls due to cleavage by the ligand-activated ribozyme 42 and 45, the concentration of protein ligand 42 falls. When the concentration of protein 42 falls below that at which the regulatable ribozyme molecules 45 are all occupied, the rate of ribozyme cleavage will begin to fall off.

By selecting for differing regulatable ribozyme-ligand affinities, the appropriate level of regulation of ribozyme-mediated destruction of the target RNA can be achieved for any given situation.

Figure 2B:
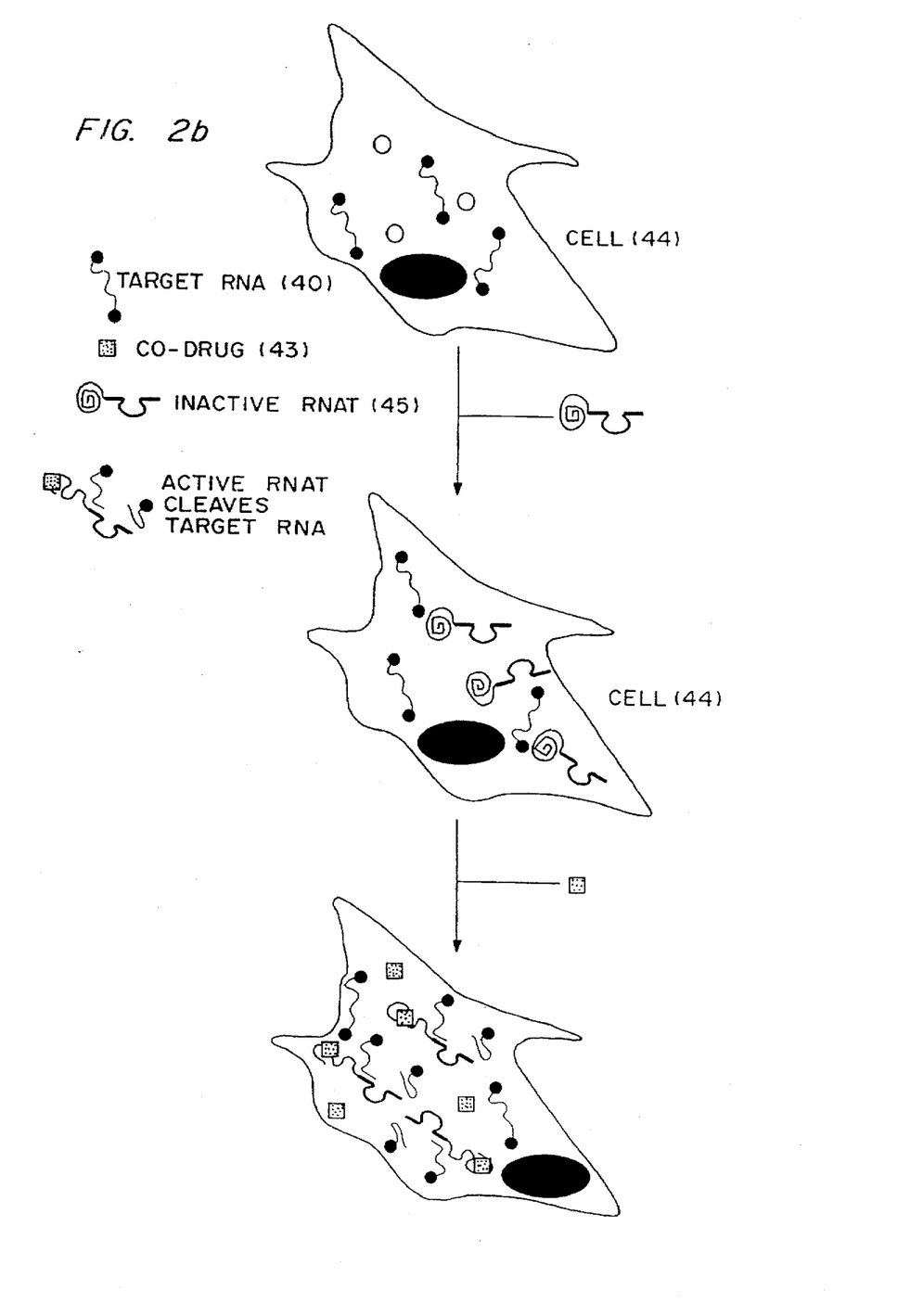
FIG. 2B is a system where the ribozyme is active against the target RNA only when a co-drug is also present which binds to the ribozyme.

FIG. 2B depicts a situation in which the ribozyme 45 is only active when bound to an exogenously supplied co-drug ligand 43 and then cleaves target 40 in cell 44.

EXAMPLE 2

Inhibition of Cleavage of HBV Substrate by Cibacron Blue Dye

Figure 3A:
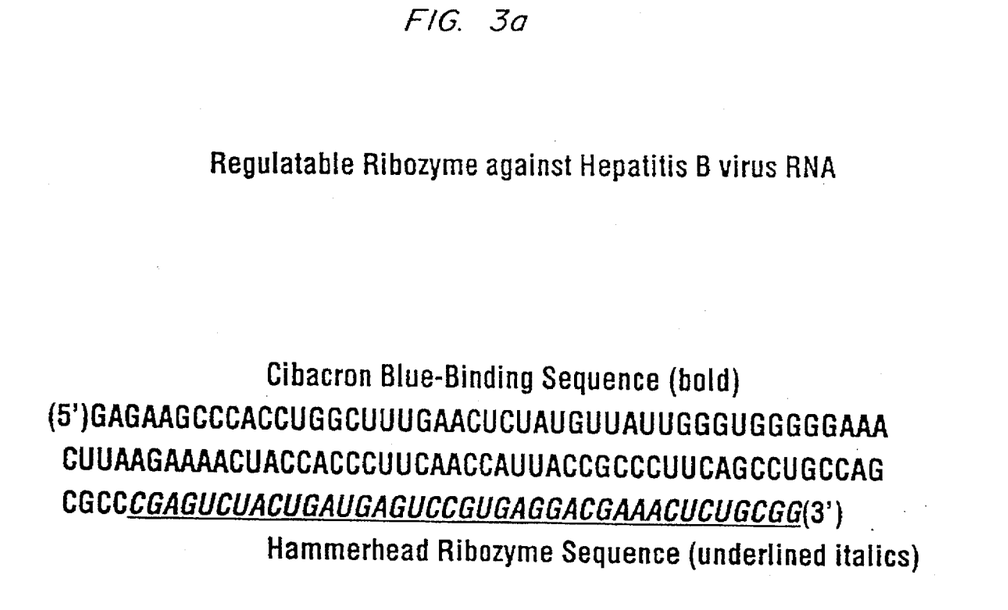
FIG. 3A shows the sequence (138 nucleotides) of a regulatable ribozyme which was constructed by synthesizing a DNA oligonucleotide which contains a Cibacron Blue (CB) dye-binding sequence (99 nt) adjacent to a sequence for a hammerhead ribozyme (39 nt) against a hepatitis B virus (HBV) surface antigen (HBsAg) mRNA (SEQUENCE ID NO.1).

FIG. 3A shows the sequence (138 nucleotides) of a regulatable ribozyme which was constructed by synthesizing a DNA oligonucleotide which contains a Cibacron Blue (CB) dye-binding sequence (99 nt) (Ellington and Szostak, 1990) adjacent to a sequence for a hammerhead ribozyme (39 nt) against a hepatitis B virus (HBV) surface antigen (HBsAg) mRNA (SEQUENCE ID. NO.1). In vitro transcription of this oligonucleotide with T7 RNA polymerase generated a single RNA molecule corresponding to the CB-binding and hammerhead sequences.

Figure 3B:
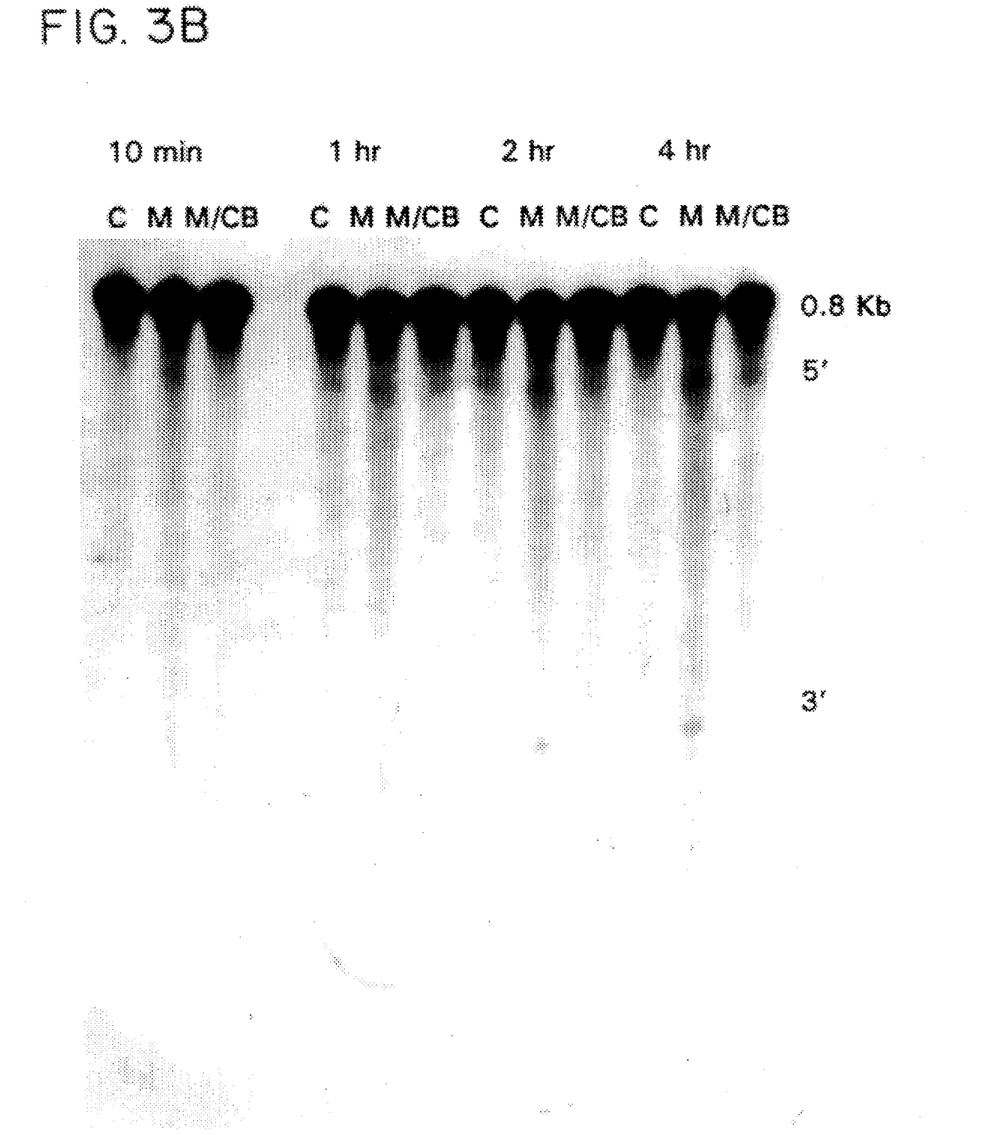
FIG. 3B shows a 4% polyacrylamide electrophoretic gel run in 1X TBE at 800 volts used for testing the ribozyme for activity in cleaving the HbsAg message in the absence and presence of CB. The ratio of substrate (an 837 nucleotide RNA corresponding to the pre-S2/S region of the HBsAg mRNA) to ribozyme was 1:4. Lanes 1–3, 4–6, 7–9, and 10–12 represent reaction times of ribozyme with substrate of 0.5, 1, 2.5, and 4 hours, respectively. Lanes 1, 4, 7, and 10 are control reactions containing ribozyme, substrate and EDTA. Lanes 2, 5, 8 and 11 are reactions of ribozyme and substrate in the presence of $Mg^{2++}$, demonstrating increased cleavage over time. Lanes 3, 6, 9, and 12 are reactions of ribozyme and substrate in the presence of $Mg^{++}$ and Cibacron blue, a ligand bound by the ribozyme sequence.

This molecule was tested for activity in cleaving the HBsAg message in the absence and presence of CB. FIG. 3B shows a 4% polyacrylamide electrophoretic gel run in 1X TBE at 800 volts. The ratio of substrate (an 837 nucleotide RNA corresponding to the pre-S2/S region of the HBsAg mRNA) to ribozyme was 1:4. Lanes 1–3, 4–6, 7–9, and 10–12 represent reaction times of ribozyme with substrate of 0.5, 1, 2.5, and 4 hours, respectively. Lanes 1, 4, 7, and 10 are control reactions containing ribozyme, substrate and EDTA. Lanes 2, 5, 8 and 11 are reactions of ribozyme and substrate in the presence of $Mg^{2+}$, demonstrating increased cleavage over time. Lanes 3, 6, 9, and 12 are reactions of ribozyme and substrate in the presence of $Mg^{++}$ and cibacron blue, a ligand bound by the ribozyme sequence. Lanes 9 and 12 clearly reveal inhibition of cleavage in the presence of the ligand compared to reactions without the ligand, lanes 8 and 11, respectively.

EXAMPLE 3

Inducible Transcription or Translation Vectors

The system's utility can be extended beyond direct medical applications into more basic research applications. FIGS. 4A–D are schematics of several additional uses of this technology to regulate expression of genes.

Figure 4A:
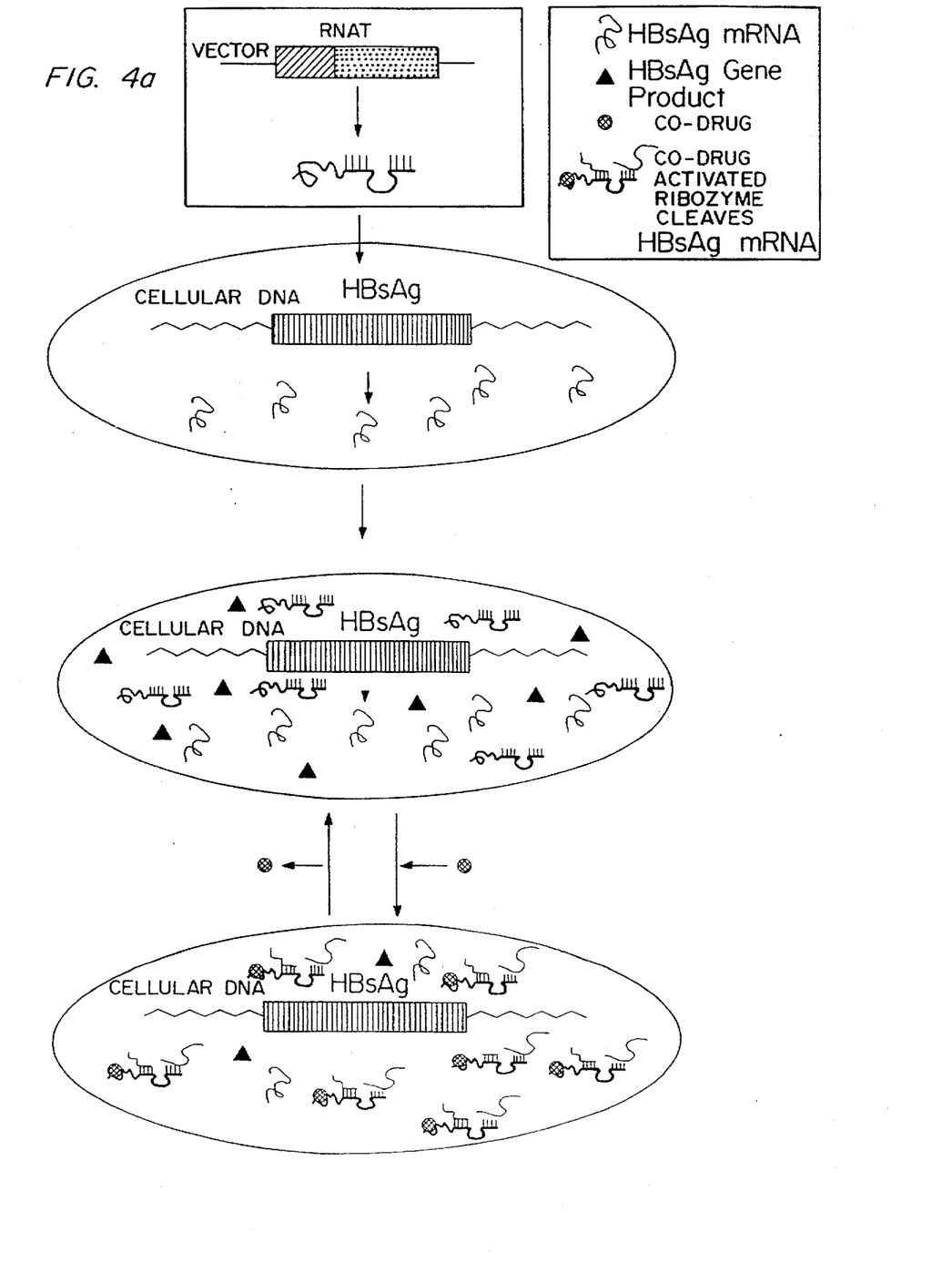
FIG. 4A is a schematic of the use of a co-drug activated ribozyme to cleave HBsAg only in the presence of the co-drug.
Figure 4B:
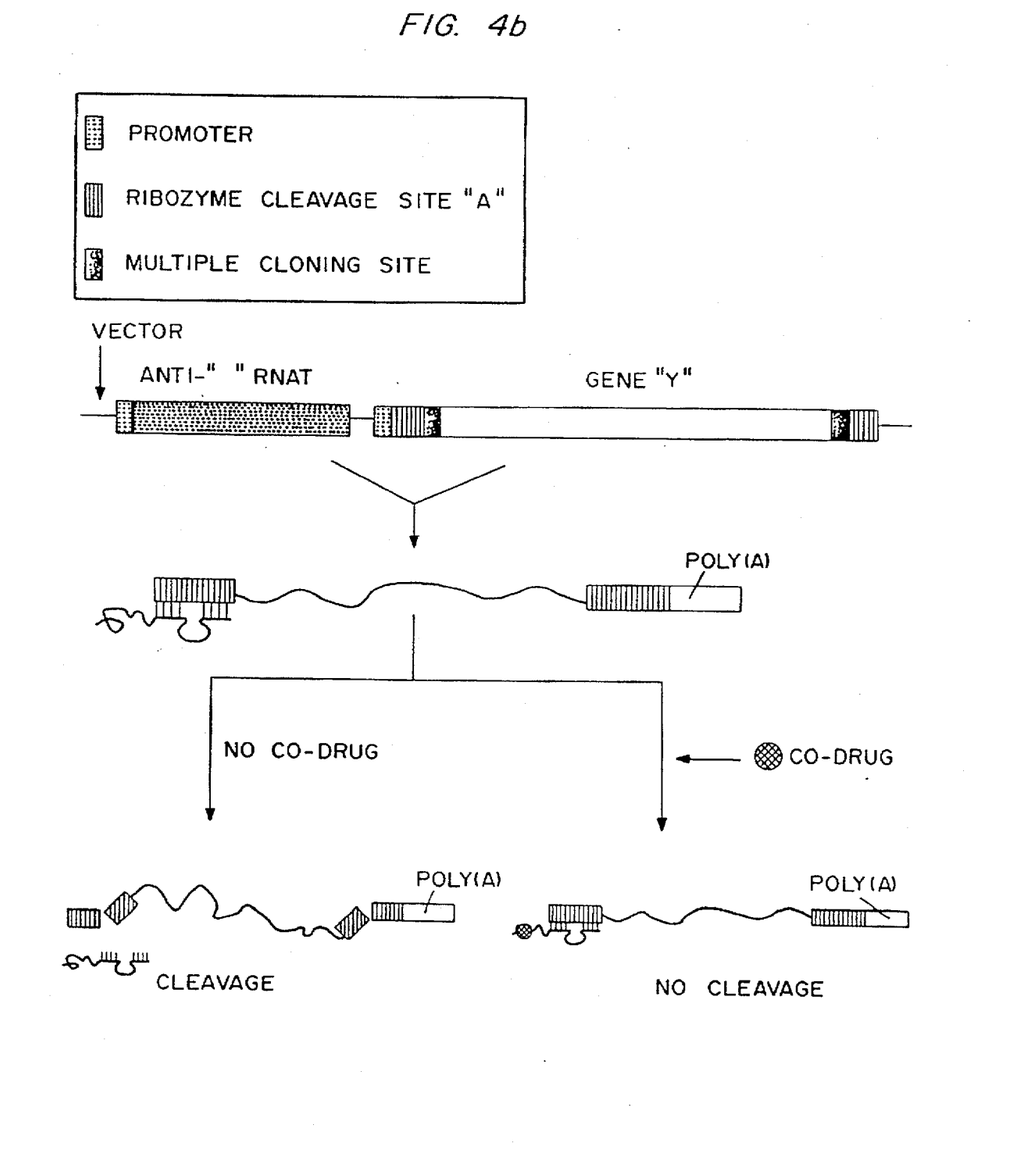
FIG. 4B is a schematic of an expression vector is constructed in which a gene for a regulatable ribozyme against a sequence is placed under control of a constitutive promoter along with the identical promoter controlling expression of any gene cloned into the multiple cloning site, followed by the sequence controlling ribozyme activity, followed by a multiple cloning site, followed by the sequence controlling ribozyme activity again, followed by a multiple cloning site, followed by the sequence controlling ribozyme activity again, followed by the polyadenylation signal.

In a first scheme, shown in FIG. 4A, one can select for a co-drug responsive ribozyme against an endogenous gene, or against a gene to be introduced subsequently into the cell by transfection of a plasmid or infection with a virus, or a gene present on the same vector as the ribozyme and the expression of which one wishes to regulate, as also depicted in FIG. 4B. For example, a synthetic gene 50 coding for a ribozyme 52 against the hepatitis B virus surface antigen (HBsAg) mRNA 54, which has been selected to be active and to cleave the HBsAg message only in the presence of a co-drug 56 which is readily taken up by cells, can be introduced into HBsAg-producing cells on a transient or stable expression plasmid 58. The steady state level of HBsAg message and protein can be quantitated readily by slot blot and ELISA, respectively. Upon addition to the medium of the co-drug 56, the cells should take it up where it acts to turn on the ribozyme 52, which now cleaves the HBsAg message 54, resulting in decreased RNA and protein levels. Upon removal of co-drug 56 from the medium the ribozyme should return to the inactive conformation and the transcript and protein levels rise again to their steady state levels.

In the system depicted in FIG. 4B, a transient or stable expression vector 60 is constructed in which a gene 62 for a regulatable ribozyme 64 against a sequence 66 is placed under control of a constitutive promoter 68. On the same plasmid 60 is the identical promoter 68 controlling expression of any gene 70 cloned into the multiple cloning site 72. Following the promoter 68 is the sequence 74, followed by a multiple cloning site 72, followed by the sequence 74 again, followed by a multiple cloning site 72, followed by the sequence 74 again, followed by the polyadenylation signal 76. Any gene 70 cloned into the multiple cloning site 72 will be transcribed to yield an mRNA 78 with the sequence 74 at the 5' terminus, upstream to the AUG start site 70a, followed by the coding region of gene 70, and the sequence 74 at the 3' end, between the stop codon 70b and the poly(A) tail 76. If the regulatable ribozyme 62 is inactive in the presence of co-drug 78, then introduction of the vector 60 into a cell in the absence of this co-drug 78 will result in transcription of both the active ribozyme against gene 70 mRNA and gene 70. However, the gene 70 message will be cleaved by the ribozyme 62 both the 5' and 3' 74 sites to yield pieces 74a and 74b and available for exonucleolytic attack from both ends; that is, gene 70 will be inactivated. When the co-drug 78 is added to the medium and enters the cells, the ribozyme 62 becomes inactive and the gene 70 mRNA will be transcribed and translated normally. Hence, gene 70 expression will be under the inducible control of the ribozyme.

Figure 4C:
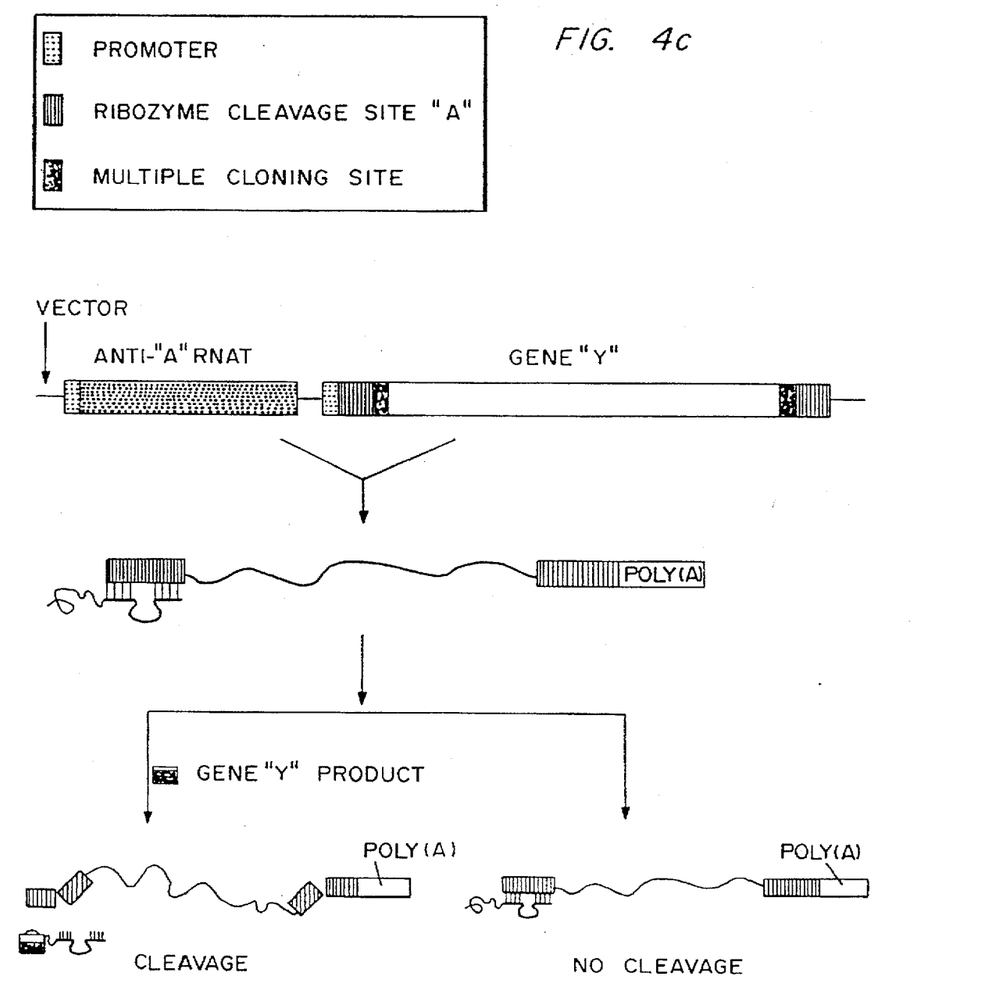
FIG. 4C is a schematic of the construction of a self-regulating expression system in which the ribozyme of FIG. 4B is regulated by the gene product.

Another system shown schematically in FIG. 4C entails the construction of a self-regulating expression system in which the ribozyme 62 of FIG. 4B is regulated by the gene product 80 of gene 70. For example, the ribozyme 62 would be active only in the presence of the protein product 80 of gene 70, at which point it would cleave at sequence 74 and inactivate the message 70, leading to decreased expression of the protein 80. As the protein level falls, more ribozyme becomes inactive and the level of gene 70 message increases.

Figure 4D:
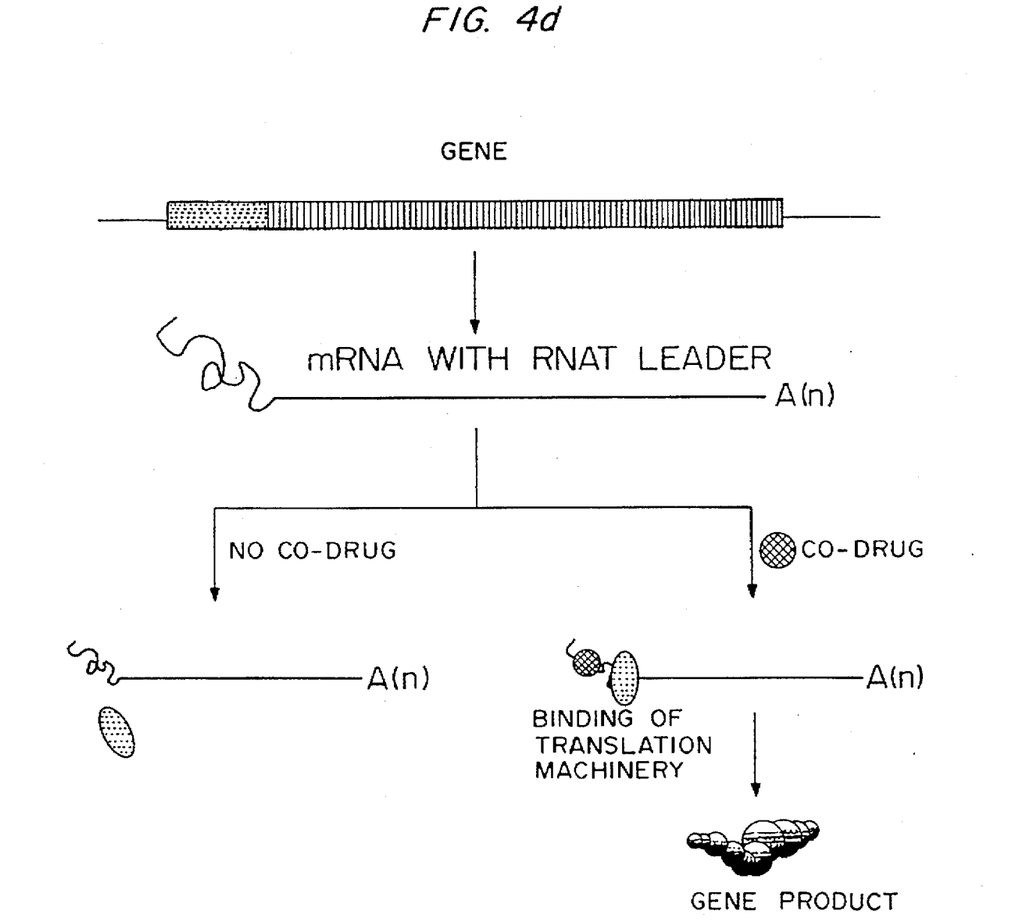
FIG. 4D is a schematic of where the regulatable ribozyme leader sequence in the absence of the co-drug interferes with the mRNAs ability to be translated and where binding of the co-drug to the leader sequence relieves this inhibition and translation can occur.

By adding a random sequence at the beginning of a transcript, one can select for an mRNA which is translationally active or inactive due to binding of the ligand. The co-drug either promotes or inhibits the formation of a structure at the 5' end of the message, thereby blocking translation by hindering accessibility to the transcript of any of a number of translational factors or by interfering with binding to the ribosome. FIG. 4D depicts where the regulatable ribozyme 82 leader sequence 84 in the absence of a co-drug 86 interferes with the mRNA 70 ability to be translated. However, when the co-drug 86 is present, its binding to the leader sequence 84 relieves this inhibition and translation can occur. This construct allows inducible translation of a message independent of its transcription, yielding the gene product 88.

Modifications and variations will be obvious to those skilled in the art from the foregoing detailed description. Such modifications and variations are intended to come within the scope of the appended claims.

We claim:

1. A regulatable ribozyme molecule comprising a ribozyme sequence which cleaves a separate targeted RNA molecule and a RNA sequence which binds to a ligand, wherein binding of the ligand alters the activity of the ribozyme against the targeted RNA,
    wherein the regulatable ribozyme molecule is made by the steps of
    providing a random nucleotide sequence of between 20 and 100 nucleotides in length which is to be linked to a sequence with ribozyme activity which cleaves a targeted RNA molecule,
    amplifying the random sequence under conditions promoting mutation of the random sequence, wherein mutation of the random sequence results in mutated sequences,
    exposing the mutated sequences to a ligand which is to be used to modify the activity of the ribozyme under conditions favorable to binding of the ribozyme to the ligand,
    removing mutated sequences not binding to the ligand,
    repeating the amplification and binding steps until mutated sequences are obtained which bind to the ligand,
    linking each of the mutated sequences which bind to the ligand to the ribozyme sequence to form ribozyme-ligand binding sequences,
    exposing the ribozyme ligand binding sequences to ligand, and
    screening for alteration of the ribozyme activity when ligand is bound and when ligand is not bound to the ligand binding sequence.

2. The ribozyme molecule of claim 1 wherein the ligand is selected from the group consisting of nucleic acid molecules, proteins polysaccharides, sugars, organic molecules and inorganic molecules.

3. The ribozyme molecule of claim 1 wherein the ribozyme is derived from a ribozyme selected from the group consisting of hammerhead ribozymes, axehead ribozymes, newt satellite ribozymes, Tetrahymena ribozymes, and RNAase P.

4. The ribozyme molecule of claim 1 wherein the ribozyme is an external guide sequence for RNAase P.

5. The ribozyme molecule of claim 1 wherein the ribozyme is inactivated when the ligand is bound to the molecule.

6. The ribozyme molecule of claim 1 wherein the ribozyme is activated when the ligand is bound to the molecule.

7. The ribozyme molecule of claim 1 wherein the ligand is exogenously administered to cells containing the regulatable ribozyme molecule.

8. The ribozyme molecule of claim 2 wherein the ligand is a product found in cells and the ribozyme activity is altered by binding to the ligand within the cells.

9. The ribozyme molecule of claim 3 wherein the ribozyme is derived from a hammerhead ribozyme.

10. A nucleic acid molecule encoding a regulatable ribozyme and a gene.

11. The molecule of claim 10 further comprising nucleic acid sequence adjacent to the gene, wherein the sequence is a substrate for the ribozyme.

12. The molecule of claim 10 further comprising a promoter and a multiple cloning site, wherein expression of the regulatable ribozyme or the gene is under control of the promoter, and wherein the multiple cloning site is adjacent to the gene.

13. The molecule of claim 10 wherein the gene encodes a product which modulates the activity of the ribozyme.

14. The molecule of claim 11 wherein the sequence is 5' and 3' to the gene.

15. A method of making a regulatable ribozyme molecule comprising a ribozyme sequence which cleaves a separate targeted RNA molecule and a RNA sequence which binds to a ligand, wherein binding of the ligand alters the activity of the ribozyme against the targeted RNA, comprising the steps of
    providing a random nucleotide sequence of between 20 and 100 nucleotides in length which is to be linked to a sequence with ribozyme activity which cleaves a targeted RNA molecule,
    amplifying the random sequence under conditions promoting mutation of the random sequence, wherein mutation of the random sequence results in mutated sequences,
    exposing the mutated sequences to a ligand which is to be used to modify the activity of the ribozyme under conditions favorable to binding of the ribozyme to the ligand,
    removing mutated sequences not binding to the ligand,
    repeating the amplification and binding steps until mutated sequences are obtained which bind to the ligand,
    linking each of the mutated sequences which bind to the ligand to the ribozyme sequence to form ribozyme-ligand binding sequences,
    exposing the ribozyme-ligand binding sequences to ligand, and
    screening for alteration of the ribozyme activity when ligand is bound and when ligand is not bound to the ligand binding sequence, wherein alteration of ribozyme activity identifies a ribozyme-ligand binding sequence as a regulatable ribozyme molecule.

16. The method of claim 15 wherein the ribozyme is derived from a hammerhead ribozyme.

17. A method for controlled cleavage of a target RNA molecule in vitro or in an isolated cell comprising providing at the site where the target RNA molecule is to be cleaved a regulatable ribozyme molecule comprising a ribozyme sequence which cleaves the target RNA molecule and a ligand binding sequence which binds to a ligand, wherein binding of the ligand alters the activity of the ribozyme against the target RNA, wherein cleavage of the targeted RNA molecule is controlled by the presence or absence of the ligand.

18. The method of claim 17 wherein the ligand is selected from the group consisting of nucleic acid molecules, proteins, polysaccharides, sugars, organic molecules and inorganic molecules.

19. The method of claim 17 wherein the ribozyme is derived from a ribozyme selected from the group consisting of hammerhead ribozymes, axehead ribozymes, newt satellite ribozymes, Tetrahymena ribozymes, and RNAase P.

20. The method of claim 17 wherein the ribozyme is an external guide sequence for RNAase P.

21. The method of claim 17 wherein the ribozyme is inactivated when the ligand is bound to the molecule.

22. The method of claim 17 wherein the ribozyme is activated when the ligand is bound to the molecule.

23. The method of claim 17 wherein the ligand is a product found in cells and the ribozyme activity is altered by binding to the ligand within the cells.

24. The method of claim 17 wherein the ligand is a product found in virally infected cells and the ribozyme is activated by binding to the ligand.

25. The method of claim 17 wherein the regulatable ribozyme molecule is made by the steps of providing a random nucleotide sequence of between 20 and 100 nucleotides in length which is to be linked to a sequence with ribozyme activity which cleaves a targeted RNA molecule, amplifying the random sequence under conditions promoting mutation of the random sequence, wherein mutation of the random sequence results in mutated sequences, exposing the mutated sequences to a ligand which is to be used to modify the activity of the ribozyme under conditions favorable to binding of the ribozyme to the ligand, removing mutated sequences not binding to the ligand, repeating the amplification and binding steps until mutated sequences are obtained which bind to the ligand, linking each of the mutated sequences which bind to the ligand to the ribozyme sequence to form ribozyme-ligand binding sequences, exposing the ribozyme-ligand binding sequences to ligand, and screening for alteration of the ribozyme activity when ligand is bound and when ligand is not bound to the ligand binding sequence.

26. The method of claim 17 wherein the regulatable ribozyme molecule is made by the steps of providing a random nucleotide sequence of 20 to 100 nucleotides linked to the ribozyme sequence, amplifying the random sequence under conditions promoting mutation of the random sequence, wherein mutation of the random sequence results in mutated sequences, exposing the mutated sequences to the ligand under conditions favorable to binding of the mutated sequences to the ligand, removing mutated sequences not binding to the ligand, repeating the amplifying and exposing steps until mutated sequences are obtained which bind to the ligand, wherein the mutated sequences which bind to the ligand are ligand binding sequences and wherein the ligand binding sequences and the ribozyme sequence together are ribozyme-ligand binding molecules, exposing the ribozyme-ligand binding molecules to ligand, and screening for alteration of the ribozyme activity when ligand is bound and when ligand is not bound to the ligand binding sequence, wherein alteration of ribozyme activity identifies a ribozyme-ligand binding sequence as a regulatable ribozyme molecule.

27. The method of claim 19 wherein the ribozyme is derived from a hammerhead ribozyme.

28. A method of making a regulatable ribozyme molecule comprising a ribozyme sequence which cleaves a separate target RNA molecule and a ligand binding sequence which binds to a ligand, wherein binding of the ligand alters the activity of the ribozyme, comprising the steps of providing a random nucleotide sequence of 20 to 100 nucleotides linked to the ribozyme sequence, amplifying the random sequence under conditions promoting mutation of the random sequence, wherein mutation of the random sequence results in mutated sequences, exposing the mutated sequences to the ligand under conditions favorable to binding of the mutated sequences to the ligand, removing mutated sequences not binding to the ligand, repeating the amplifying and exposing steps until mutated sequences are obtained which bind to the ligand, wherein the mutated sequences which bind to the ligand are ligand binding sequences and wherein the ligand binding sequences and the ribozyme sequence together are ribozyme-ligand binding molecules, exposing the ribozyme-ligand binding molecules to ligand, and screening for alteration of the ribozyme activity when ligand is bound and when ligand is not bound to the ligand binding sequence, wherein alteration of ribozyme activity identifies a ribozyme-ligand binding sequence as a regulatable ribozyme molecule.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 138 base pairs
        ( B ) TYPE: nucleic acid
        ( C ) STRANDEDNESS: single
        ( D ) TOPOLOGY: linear     ( i i ) MOLECULE TYPE: RNA (genomic)

( i i i ) HYPOTHETICAL: NO

( i v ) ANTI-SENSE: NO

( v i ) ORIGINAL SOURCE:
        ( A ) ORGANISM: Synthetic     ( i x ) FEATURE:
        ( A ) NAME/KEY: misc_feature
        ( B ) LOCATION: 1..99
        ( D ) OTHER INFORMATION: /note= "Cibacron Blue-Binding Sequence"

-continued ( i x ) FEATURE:
    ( A ) NAME/KEY: misc_feature
    ( B ) LOCATION: 100..138
    ( D ) OTHER INFORMATION: /note= "Hammerhead Ribozyme Sequence"

( x i ) SEQUENCE DESCRIPTION: SEQ ID NO:1:

| | | | | | | |
|---|---|---|---|---|---|---|
| GAGAAGCCCA | CCUGGCUUUG | AACUCUAUGU | UAUUGGGUGG | GGGAAACUUA | AGAAAACUAC | 6 0 |
| CACCCUUCAA | CCAUUACCGC | CCUUCAGCCU | GCCAGCGCCC | GAGUCUACUG | AUGAGUCCGU | 1 2 0 |
| GAGGACGAAA | CUCUGCGG | | | | | 1 3 8 |